United States Patent [19]

Tóth et al.

[11] Patent Number: 5,118,687
[45] Date of Patent: Jun. 2, 1992

[54] 1-OXA-2-OXO-8-AZASPIRO(4,5)DECANE DERIVATIVES, PHARMACEUTICAL COMPOSITIONS CONTAINING THEM AND PROCESS FOR PREPARING SAME

[75] Inventors: Edit Tóth; József Törley; László Szporny; Béla Kiss; Egon Kárpáti; Éva Pálosi; Dóra Groó; István Laszlovszky; Zsolt Szombathelyi; Ádám Sarkadi; Anikó Gere; Katalin Csomor; Mihály Bodó; Judit Laszy; Zsolt Szentirmay, all of Budapest, Hungary

[73] Assignee: Richter Gedeon Vegyeszeti Gyar Rt., Budapest, Hungary

[21] Appl. No.: 566,275

[22] Filed: Aug. 10, 1990

[30] Foreign Application Priority Data

Aug. 10, 1989 [HU] Hungary ............... 4095/89

[51] Int. Cl.$^5$ .................. C07D 491/10; A61K 31/44
[52] U.S. Cl. ....................... 514/278; 546/19
[58] Field of Search ............. 546/19; 514/278

[56] References Cited
U.S. PATENT DOCUMENTS 3,864,348  2/1975  Regnier et al. ............. 546/19

OTHER PUBLICATIONS

Jones et al. "Substituted 1,1'-diphenyl . . . " J. Med. Chem. 14(2) 161-164 (1971).

Primary Examiner—C. Warren Ivy
Assistant Examiner—Celia Chang
Attorney, Agent, or Firm—Herbert Dubno; Jonathan Myers

[57] ABSTRACT

The invention relates to novel compounds 1-oxa-2-oxo-8- of the formula (I),

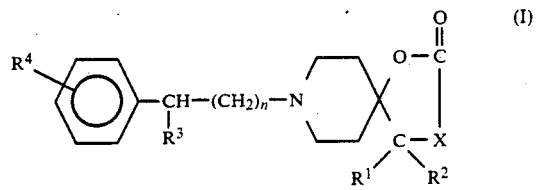

wherein X means oxygen or an >NR group, wherein
  R stands for hydrogen, a $C_{1-12}$alkyl, $C_{3-6}$cycloalkyl, carbocyclic $C_{6-10}$aryl or carbocyclic $C_{6-10}$aryl-$C_{1-4}$alkyl group, the latter two groups are optionally substituted on their aromatic moiety by one or more, same or different halogen(s), one or more $C_{1-4}$alkyl or $C_{1-4}$alkoxy group(s);

$R^1$ and $R^2$ together represent a methylene group or, when X stands for an >NR group, wherein R is as defined above, one of $R^1$ and $R^2$ may represent a hydroxyl group whereas the other is a methyl group;

$R^3$ stands for hydrogen or a phenyl group optionally substituted by one or more halogen(s), one or more $C_{1-4}$alkyl or $C_{1-4}$alkoxy or hydroxyl group(s);

$R^4$ means hydrogen, one or more halogen(s), $C_{1-4}$alkyl, $C_{1-4}$alkoxy, hydroxyl or trihalomethyl group(s); and n is 1, 2 or 3 as well as their acid addition and quaternary ammonium salts.

13 Claims, No Drawings

1-OXA-2-OXO-8-AZASPIRO(4,5)DECANE DERIVATIVES, PHARMACEUTICAL COMPOSITIONS CONTAINING THEM AND PROCESS FOR PREPARING SAME

The invention relates to novel, therapeutically active 1-oxa-2-oxo-8-azaspiro[4,5]decane derivatives of the formula (I),

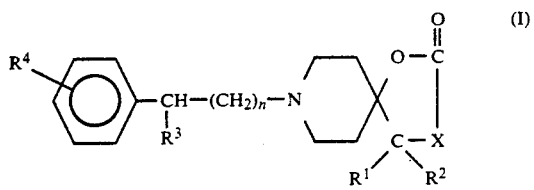

wherein
X means oxygen or an >NR group, wherein
R stands for hydrogen, a $C_{1-12}$alkyl, $C_{3-6}$cycloalkyl, carbocyclic $C_{6-10}$aryl or carbocyclic $C_{6-10}$aryl-$C_{1-4}$alkyl group, the two latter groups are optionally substituted on their aromatic moiety by one or more, same or different halogen(s), one or more $C_{1-4}$alkyl or $C_{1-4}$alkoxy group(s);
$R^1$ and $R^2$ together represent a methylene group or, when X stands for an >NR group, wherein R is as defined above, one of $R^1$ and $R^2$ may represent a hydroxyl group whereas the other is a methyl group;
$R^3$ stands for hydrogen or a phenyl group optionally substituted by one or more halogen(s), one or more $C_{1-4}$alkyl or $C_{1-4}$alkoxy or hydroxyl group (s);
$R^4$ means hydrogen, one or more halogen(s), $C_{1-4}$alkyl, $C_{1-4}$alkoxy, hydroxyl or trihalomethyl group(s); and
n is 1, 2 or 3
as well as their acid addition and quaternary ammonium salts and pharmaceutical compositions containing these compounds.

The invention also relates to a process for the preparation of the above compounds and compositions as well as to a method of treatment. The latter comprises administering a therapeutically effective amount of a compound of formula (I) or a pharmaceutically acceptable acid addition or quaternary ammonium salt thereof to of a patient.

The compounds of the formula (I) may exist in various stereoisomeric forms such as geometrical isomers as well as racemates, individual optical isomers and their mixtures, all of which may occur in the form of various solvates and hydrates. All these compounds and mixtures are within the scope of the invention.

A number of therapeutically useful 1-oxa-2-oxo-3,8-diazaspiro[4,5]decane derivatives have been described in the literature. Such compounds are reported e.g. in the following publications: C.A. 71, 91359d (1969); C.A. 78, 719668t (1973); C.A. 78, 23876q (1973); C.A. 81, 33153c and 105368b (1974); C.A. 95, 1616765e (1981); as well as in the DE patent specifications Nos. 2,013,729, 2,013,668 and 2,163,000; in the Belgian patent specifications Nos. 775,984, 774,170, 786,631 and 825,444; in the British patent specification No. 1,100,281; in the published Dutch patent application No. 7,214,689 as well as in the U.S. Pat. Nos. 3,555,033, 3,594,386, 4,244,961 and 4,255,432.

A substantial difference between the compounds of formula (I) according to the invention and the similar derivatives known up to the present appears in the nature of the substituents bound in position 4 and optionally in position 3 of the spirodecane skeleton.

According to an other aspect of the invention, there is provided a process for the preparation of compounds of the formula (I) as well as their acid addition and quaternary ammonium salts, which comprises a) reacting a 2-oxo-3,8-diazaspiro[4,5]decane derivative of the formula (II),

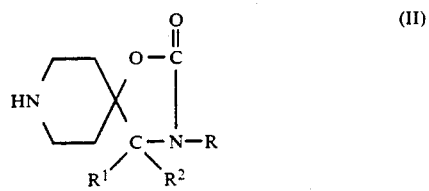

wherein R, $R^1$ and $R^2$ are as defined above, with a phenylalkane derivative of the formula (III),

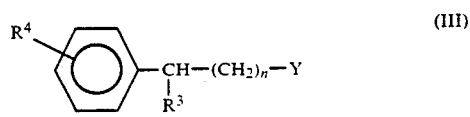

wherein $R^3$, $R^4$ as well as n are as defined above and Y means halogen, a $C_{1-4}$alkylsulfonyloxy or arylsulfonyloxy group,
to obtain compounds of the formula (I), wherein X stands for an >NR group and R, $R^1$, $R^2$, $R^3$, $R^4$ as well as n are as defined above; or b) reactinga 4-ethynyl-4-hydroxypiperidine derivative of the formula (IV),

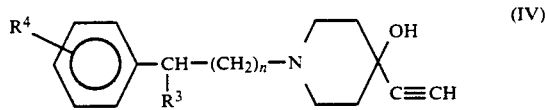

wherein $R^3$, $R^4$ and n are as defined above, with an isocyanate of the formula R—NCO, wherein R is as defined above, and $\alpha$) cyclizing in an acidic medium the obtained 4-carbamoyloxy-4-ethynylpiperidine derivative of the formula (V),

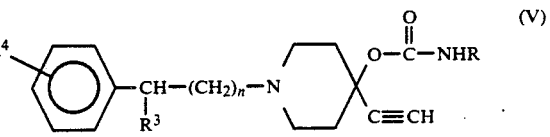

wherein R, $R^3$, $R^4$ and n are as defined above and reacting with water the obtained salt of the 2-imino-1,3-dioxolane derivative of the formula (VI),

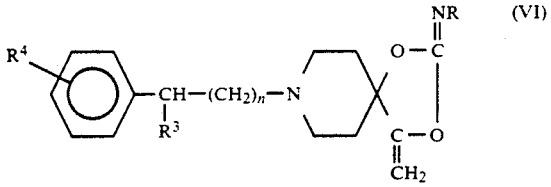

wherein R, $R^3$, $R^4$ and n are as defined above, to obtain compounds of the formula (I), wherein $R^1$ and
$R^2$ together represent a methylene group, X means oxygen,
and R, $R^3$, $R^4$ as well as n are as defined above, or β) cyclizing in a basic medium the obtained compound of the formula (V), wherein R, $R^3$, $R^4$ and n are as defined above,
to obtain compounds of the formula (I), wherein X means an >NR group, $R^1$ and $R^2$ together represent a methylene group and R, $R^3$, $R^4$ as well as n are as defined above;

c) cyclizing in an acidic medium a 4-carbamoyloxy-4-ethynylpiperidine derivative of the formula (V) above, wherein R, $R^3$, $R^4$ and n are as defined above, and reacting with water the obtained salt of the 2-imino-1,3-dioxolane derivative of the formula (VI), wherein R, $R^3$, $R^4$ and n are as defined above,
to obtain compounds of the formula (I), wherein X means oxygen, $R^3$, $R^4$ as well as n are as defined above and $R^1$ together with $R^2$ stands for a methylene group; or d) cyclizing in the presence of a base a 4-carbamoyloxy-4-ethynylpiperidine derivative of the formula (V), wherein R, $R^3$, $R^4$ and n are as defined above, to obtain compounds of the formula (I), wherein X means an >NR group, $R^1$ together with $R^2$ stands for a methylene
group and R, $R^3$, $R^4$ as well as n are as defined above; or e) reacting a 4-acetyl-4-hydroxypiperidine derivative of the formula (VII),

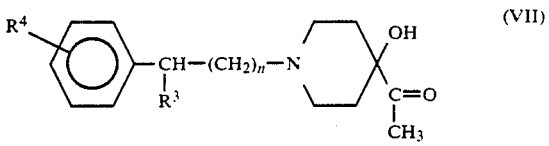

wherein $R^3$, $R^4$ and n are as defined above, with an isocyanate of the formula R—NCO, wherein R is as defined above, and cyclizing the thus formed 4-acetyl-4-carbamoyloxypiperidine derivative of the formula (VIII)

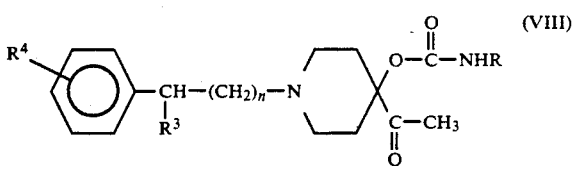

wherein R, $R^3$, $R^4$ and n are as defined above, to obtain compounds of the formula (I), wherein X means an >NR group, one of $R^1$ and $R^2$ stands for a hydroxyl group and the other is a methyl group, and R, $R^3$, $R^4$ as well as n are as defined above; or f) cyclizing a 4-acetyl-4-carbamoyloxypiperidine derivative of the formula (VIII), wherein R, $R^3$, $R^4$ and n are as defined above,
to obtain compounds of the formula (I), wherein X means an >NR group, one of $R^1$ and $R^2$ stands for a hydroxyl group, the other is methyl group and R, $R^3$, $R^4$ as well as n are as defined above, then, if desired, reacting a thus prepared compound of the formula (I), wherein X means oxygen, $R^1$ and $R^2$ together stand for a methylene group, $R^3$, $R^4$ and n are as defined above, with an amine of the formula R—NH$_2$, wherein R is as defined above, to prepare a compound of the formula (I), wherein X means an >NR group, one of $R^1$ and $R^2$ stands for a hydroxyl group, the other is methyl group and R, $R^3$, $R^4$ as well as n are as defined above; or transforming a thus prepared compound of the formula (I), wherein X, R, $R^1$, $R^2$, $R^3$, $R^4$ and n are as defined in the preamble, to an other compound of the formula (I) falling within the scope of the formula (I); or reacting with an acid a thus prepared compound of the formula (I), wherein X, R, $R^1$, $R^2$, $R^3$, $R^4$ and n are as defined above to give its acid addition salt or treating with a base a compound of the formula (I), wherein X, R, $R^1$, $R^2$, $R^3$, $R^4$ and n are as defined above obtained as a salt, to liberate the base form thereof or converting a thus prepared compound of the formula (I), wherein X, R, $R^1$, $R^2$, $R^3$, $R^4$ and n are as defined above, to its quaternary ammonium salt.

In the process a) according to the invention, a 2-oxo-3,8-diazaspiro[4,5]decane derivative of the formula (II) is reacted with a phenylalkane derivative of the formula (III), wherein Y means a leaving group, e.g. a mesyloxy or tosyloxy group, or a halogen, preferably chlorine or bromine. This reaction is preferably carried out in an inert organic solvent, in the presence of a base being capable to bind the acid liberated in the reaction. Various solvents, such as aliphatic alkanols, e.g. ethanol, isopropanol, butanol; aromatic hydrocarbons, e.g. chlorobenzene, toluene; ethers, e.g. dibutyl ether or dioxane; tertiary aliphatic acid amides such as dimethylformamide or dimethylacetamide; ketones, e.g. acetone, methyl ethyl ketone or methyl isobutyl ketone or the mixtures of the above solvents may be used; as acid binding agents inorganic or tertiary organic bases, e.g. alkaline or earth alkaline metal carbonates or hydrogen carbonates as well as triethylamine, dimethylaniline or pyridine may be employed though an excess of the compound of formula (II) can also be used for the same purpose. This reaction is accomplished at a temperature between room temperature and the boiling point of the reaction mixture, optionally in the presence of a catalyst. Suitable catalysts are e.g. the alkali metal iodides. The reaction is preferably performed under an inert gas such as nitrogen or argon.

In the first step of process b) according to the invention a 4-ethynyl-4-hydroxpiperidine derivative of the formula (IV) is brought into reaction with an isocyanate of the formula R—NCO in a manner known per se [Houben-Weyl: Methoden der Organischen Chemie Vol. VIII/3, pages 137 to 147 (1952)] to give a 4-carbamoyloxy-4-ethynylpiperidine derivative of the formula (V). For preparing compounds of the formula (I) containing oxygen as X, the compound of the formula (V) is cyclized in an acidic medium according to step α), then the thus-formed 2-imino-1,3-dioxolane derivative of the formula (VI) obtained as a salt is reacted with water; or, for preparing compounds of the formula (I)

containing an >NR group as X, the compound of formula (V) is cyclized in a basic medium according to step β).

The cyclization of step (α) is carried out in an inert organic solvent (i.e. in a solvent which is inert under the reaction conditions), in the presence of a suitable acid, preferably in the presence of a dry hydrogen halide. Aliphatic or alicyclic ethers such as diethyl ether, dipropyl ether, diisopropyl ether, dibutyl ether, tetrahydrofuran or dioxane as well as lower aliphatic carboxylic acids, e.g. acetic or propionic acid, may be employed.

As a hydrogen halide, hydrogen chloride, bromide, iodide or fluoride, preferably hydrogen chloride or bromide, are used. After treating the thus formed 2-imino-1,3-dioxolane hydrohalide salt with water, the 1-oxa-2-oxo-8-azaspiro[4,5]decane derivative of the formula (I) is obtained as an acid addition salt from which, if desired, the base can be liberated in a manner known per se.

The cyclization of step β) is realized in the presence of a base. Alkali metal acetates, carbonates, alkoxides, hydroxides and/or tertiary organic bases, e.g. pyridine, tripropylamine or picoline, may be used as basic catalysts in the cyclization; the organic bases may also serve as solvents for the reaction. Further suitable solvents are aliphatic alcohols, e.g. methanol, ethanol, propanol or butanol; aliphatic, alicyclic or aromatic hydrocarbons, e.g. hexane, cyclohexane, benzene, toluene or xylene; acid amides, e.g. dimethylformamide or N-methyl-2-pyrrolidone; ethers such as dibutyl ether or dioxane; nitriles such as acetonitrile; sulfoxides, e.g. dimethylsulfoxide; etc. as well as the mixtures of the above solvents. The reaction may be carried out without any solvent, too, e.g. in a molten state. In order to accelerate the cyclization the temperature is suitably increased; the reaction is preferably accomplished between 40° C. and the boiling point of the reaction mixture. It is suitable to work under an inert gas such as argon or nitrogen. According to a preferred embodiment the 4-carbamoyloxy-4-ethynylpiperidine derivative of the formula (V), formed in the reaction of the 4-ethynyl-4-hydroxypiperidine derivative of the formula (IV) with the isocyanate of the formula R—NCO, is directly cyclized, without isolation, in the same reaction mixture, in the presence of a suitable base.

In the processes c) and d) of the invention the procedures discussed under steps α) and β) are followed.

In the process e) of the invention a 4-acetyl-4-hydroxypiperidine derivative of the formula (VII) is reacted with an isocyanate of the formula R—NCO and the obtained 4-acetyl-4-carbamoyloxypiperidine derivative of the formula (VIII) is cyclized. The condensation reaction according to the first step is realized in a manner known per se [Houben-Weyl: Methoden der Organischen Chemie Vol. VIII/3, pages 137 to 147 (1952)]. The obtained 4-acetyl-4-carbamoyloxypiperidine derivative of the formula (VIII) is preferably cyclized in the presence of a base. The cyclization may be carried out under the reaction conditions described for the step β) of process b). Alternatively, according to a preferred embodiment of this process, the 4-acetyl-4-carbamoyloxypiperidine derivative of the formula (VIII), obtained in the reaction of the 4-acetyl-4-hydroxypiperidine derivative of the formula (VII) with the isocyanate of formula R—NCO, is directly cyclized, without isolation, in the same reaction mixture, in the presence of a suitable base.

By using the process f) of the invention, the second step of the process e) is in principle followed.

If desired, the compounds of the formula (I) obtained by using the processes a) to f) can be transformed to other compounds being within the scope of the formula (I) in a manner known per se.

Thus, on reacting a compound of the formula (I), wherein X means oxygen and $R^1$ together with $R^2$ represents a methylene group, with an amine of the formula R—$NH_2$, compounds of the formula (I) are obtained, wherein X means an >NR group and one of $R^1$ and $R^2$ is a hydroxyl group whereas the other one means a methyl group. This reaction may be carried out in a suitable solvent or without any solvent. Convenient solvents are e.g. aliphatic, alicyclic or araliphatic alcohols such as ethanol, butanol, cyclohexanol, benzyl alcohol; aliphatic or aromatic hydrocarbons such as hexane, heptane, xylene, chlorobenzene or nitrobenzene; ethers, e.g. dioxane; ketones, e.g. di-n-butyl ketone; tertiary organic bases, e.g. picoline, triethylamine or pyridine, though an excess of the R—$NH_2$ amine may also serve as a solvent for the reaction. This procedure may be carried out at a temperature between room temperature and the boiling point of the reaction mixture, preferably under an inert gas, e.g. argon or nitrogen.

If desired, the compounds of the formula (I) containing a hydroxyl and a methyl group, respectively as $R^1$ and $R^2$, can be dehydrated to compounds of the formula (I), wherein $R^1$ and $R^2$ together represent a methylene group. The dehydration may be achieved under normal or reduced pressure by using commonly known procedures. Isocyanates, aliphatic carboxylic acids, aliphatic or aromatic carboxylic acid anhydrides, Lewis acids, sulfuric acid or aromatic sulfonic acids can be employed for the dehydration. This reaction is preferably performed in an organic solvent. Suitable solvents are e.g. aromatic hydrocarbons such as benzene, toluene or xylene; ethers such as dioxane, di-n-butyl ether; or aliphatic carboxylic acids such as acetic acid. Optionally, the water formed in the reaction may be removed by azeotropic distillation.

If desired, a water molecule can be introduced in an addition reaction into the compounds of formula (I), wherein $R^1$ and $R^2$ together stand for a methylene group to give compounds of the formula (I) containing a hydroxyl and a methyl group, respectively as $R^1$ and $R^2$. This hydration reaction is accomplished in an aqueous medium, in the presence of mineral and/or organic acids. As acids e.g. hydrogen halides, sulfuric, phosphoric, formic acid, aromatic sulfonic acids, oxalic or trifluoroacetic acid and the like may be employed. This reaction is carried out between 5° C. and the boiling point of the reaction mixture.

The compounds of the formula (I) may be converted to their acid addition salts or quaternary ammonium salts by using methods known per se. For the preparation of acid addition salts inorganic or organic acids such as hydrogen halides, e.g. hydrochloric acid and hydrobromic acid, sulfuric acid, phosphoric acids as well as formic, acetic, propionic, oxalic, glycolic, maleic, fumaric, succinic, tartaric, ascorbic, citric, malic, salicylic, lactic, benzoic, cinnamic, aspartic, glutamic, N-acetyl-aspartic or N-acetylglutamic acid as well as alkanesulfonic acids such as methanesulfonic acid or arenesulfonic acids, e.g. p-toluenesulfonic acid and the like may be used.

The salt formation can be carried out e.g. in such a way that the corresponding acid is added to the solution of the compound of formula (I) in an inert solvent, e.g. ethanol, and the salt formed is precipitated by adding preferably a water-immiscible organic solvent, e.g. ethyl ether. For the preparation of quaternary ammonium salts a lower alkyl, alkenyl or benzyl halide or an alkyl sulfate may preferably be employed. The quaternization is suitably performed in an organic solvent such as acetone, acetonitrile, ethanol or their mixtures, at a temperature range from room temperature up to the boiling point of the solvent. The acid addition or quaternary ammonium salt obtained may be isolated e.g. by filtration and, when necessary, purified by recrystallization.

Conversely, the corresponding bases can be liberated from their salts by an alkaline treatment.

A part of the starting substances used in the process of the invention are known or can be prepared by using known methods.

The compounds of the formula (III) can be prepared e.g. according to Collection Czechoslov. Chem. Commun. 38, 3879 (1973); as well as Chim. Ther. 3, 185 (1969).

The preparation of the compounds of formula (II) is described in our Hungarian patent application No. 4092/89 and the commonly assigned concurrently filed copending U.S. patent application Ser. No. 566,274.

The substances of formula (IV) may be synthesized e.g. by the ethynylation reaction of suitably substituted 4-piperidone derivatives as described e.g. in the Hungarian patent specification No. 166,769 or in Farmaco (Pavia) Ed. Sci. 12, 34 (1957).

The carbamates of the formulae (V) and (VIII), respectively are obtained e.g. by reacting a compound of the formula (IV) or (VII), respectively, with an isocyanate of the formula R—NCO under conditions commonly known in the literature [Houben-Weyl: Methoden der Organischen Chemie Vol. VIII/3, pages 137 to 147 (1952)].

The 4-acetyl-4-hydroxypiperidine derivatives of the formula (VII) can be prepared e.g. by hydrating the corresponding 4-ethynyl-4-hydroxypiperidine derivatives of formula (IV) [see e.g. in: Houben-Weyl: Methoden der Organischen Chemie Vol. VII/2 a, pages 826 to 835 (1973)] or by the alkaline treatment of the corresponding 1,3-dioxa-2-oxo-4-methylene-8-azaspiro[4,5]-decane derivatives of formula (I).

The compounds of formulae (IV), (V), (VII) and (VIII) are novel compounds, up to the present not described in the literature, which are valuable intermediates in the synthesis of the novel compounds according to the invention and in addition, they are biologically active, too.

The compounds of formula (I) as well as their stereoisomers and salts exhibit valuable pharmacological properties such as calcuim uptake-inhibiting, antihypoxic and antianoxic effects. Thus they are useful for the systemic (i.e. oral, rectal or parenteral) treatment of warm-blooded mammals (including man). They can favorably be employed for the prevention or therapeutic treatment of hypoxic brain damages of various origin such as senile dementia, Alzheimer's disease, ischemic lesions, disturbances of the cognitive function, multi-infarctual dementia, hypoxia following atheroschlerosis and the like.

The calcium uptake-inhibiting action of the novel compounds of formula (I) was studied on a rat brain synaptosomal preparation by using the method of P. H. Wu et al. [J. Neurochem. 39, 700 (1982)].

Wistar rats weighting 180 to 200 g were decapitated, their brains were collected in an ice-cold physiological saline solution, the cortex was removed and purified from the white substance. The tissue was homogenized in 10 volumes of 0.32M sucrose solution by using a glass-teflon potter. After centrifuging the homogenate at a rate of $1000 \times g$ at 4° C. for 10 minutes, the supernatant was further centrifuged at $10000 \times g$ for 20 minutes. The sediment was taken up in a 0.32M sucrose solution in such a way that the protein content of the preparation was adjusted to 20 mg/ml.

The medium (containing 112 mM of sodium chloride, 5 mM of potassium chloride, 1.3 mM of magnesium chloride, 1.2 mM of sodium dihydrogen phosphate, 1.2 mM of calcium chloride, 10 mM of glucose, 20 mM of TRIS buffer) used for the incubation was saturated with carbogen, consisting of 95% by volume of oxygen and 5% by volume of carbon dioxide, up to a pH of 7.4. After adding the test substances to the medium, the synaptosomal preparation was added in an amount corresponding to 1 mg of protein. The incubation was carried out in a final volume of 1 ml. The samples were pre-incubated at 34° C. for 20 minutes. The calcium uptake was begun by using a $^{45}CaCl_2$ solution of 75 nCi activity. Potassium chloride used for investigating the potassium-induced $^{45}Ca$ uptake was employed in 60 mM concentration whereas sodium chloride was added in the same concentration to the control samples. The incubation lasted 20 seconds. The reaction was stopped by 5 ml of a stopping solution containing 120 mM of sodium chloride, 5 mM of potassium chloride, 5 mM of EGTA and 20 mM of TRIS at pH 7.4. The samples were filtered through a Whatman GF/C filter paper and twice washed with 5 ml of a washing solution each, containing 132 mM of sodium chloride, 5 mM of potassium chloride, 1.3 mM of magnesium chloride, 1.2 mM of calcium chloride and 20 mM of IRIS at pH 7.4. (Abbreviations used above: TRIS means tris(hydroxymethyl)aminomethane; EGTA means ethylene glycol bis($\beta$-aminoethyl) ether-N,N,N',N'-tetraacetic acid).

The filter papers were put into glass cuvets, 10 ml of a scintillation liquid each were added, then the radioactivity of the samples was measured in an 1219 Rackbeta (LKB Wallace) liquid scintillation spectrophotometer.

The $IC_{50}$ values obtained by examination of the concentration/effect correlations are shown in Table I. $IC_{50}$ value means the molar concentration of the test compounds which causes 50% inhibition of the stimulated $^{45}Ca$ uptake.

TABLE I

| Compound No. | $IC_{50}$ $\mu M$ |
|---|---|
| 1 | 5.8 |
| 2 | 5.9 |
| 3 | 2.1 |
| 4 | 5.3 |
| 5 | 6.1 |

Numbers for the chemical names and abbreviations used in the Tables:
1 1-Oxa-2-oxo-3-butyl-4-methylene-8-[4,4-bis(4-fluorophenyl)butyl]-3,8-diazaspiro[4,5]decane
2 1-Oxa-2-oxo-3-tert-butyl-4-methylene-8-[4,4-bis(4-fluorophenyl)butyl]-3,8-diazaspiro[4,5]decane
3 1-Oxa-2-oxo-3-phenyl-4-methylene-8-[4,4-bis(4-fluorophenyl)butyl]-3,8-diazaspiro[4,5]decane
4 1-Oxa-2-oxo-3-cyclohexyl-4-methylene-8-[4,4-bis(4-fluorophenyl)butyl]-3,8-diazaspiro[4,5]decane

TABLE I-continued 5. 1-Oxa-2-oxo-3-butyl-4-hydroxy-4-methyl-8-[4,4-bis(4-fluorophenyl)butyl]-3,8-diazaspiro[4,5]decane hydrochloride
6. 1-Oxa-2-oxo-3,4-dimethyl-4-hydroxy-8-[2-(4-fluorophenyl)ethyl]-3,8-diazaspiro[4,5]decane
7. 1-Oxa-2-oxo-3-propyl-4-hydroxy-4-methyl-8-[2-(4-fluorophenyl)ethyl]-3,8-diazaspiro[4,5]decane
8. 1-Oxa-2-oxo-3-cyclohexyl-4-hydroxy-4-methyl-8-[2-(4-fluorophenyl)ethyl]-3,8-diazaspiro[4,5]decane
9. 1-Oxa-2-oxo-3-ethyl-4-hydroxy-4-methyl-8-[2-(4-fluorophenyl)ethyl]-3,8-diazaspiro[4,5]decane.

Abbreviations:
n: number of animals
p.o.: oral administration
i.v.: intravenous injection
S.E.: standard error The antiphypoxic effect was studied by using two methods. According to the method of C. Caillard et al. [Life Sci. 16, 1607 (1975)] the asphyxial action was determined after starvation for 16 hours on CFLP mice of both sexes weighting 24 to 26 g. Each animal was placed in a separate well-closed glass cylinder. The interval passing from closing the cylinder until the cessation of the last visible respiratory movement was registered as survival time. Animals, surviving longer by 30% than the average survival time of the control group, were considered to be protected. The test substances were administered in an oral dose of 50 mg/kg by 60 minutes before starting the examination. The results are summarized in Table II.

TABLE II

| Compound No. | Protected animals % | n |
|---|---|---|
| 6 | 60 | 10 |
| 7 | 40 | 10 |
| 8 | 60 | 10 |
| 9 | 60 | 10 |

The average survival time of the control group was $23.5 \pm 2.51$ sec ($X \pm$ S.E.)

The potassium cyanide test method was used for determination of the protective effect against the histotoxic hypoxia. A hypoxia of this type can be developed by a rapid intravenous injection of 5.0 mg/kg of potassium cyanide inducing abdominal contractions and clonic convulsions on the animals and leading to death of the animals within 2 minutes.

Male Hannover-Wistar rats weighting 160 to 170 g were used in this experiment. Animals surviving longer by 30% than the average survival time of the control group were considered to be protected. The test substances were orally administered in various doses 60 minutes before starting the examination. The $ED_{50}$ values, i.e. the dose protecting half of the treated animals from the hypoxia, were calculated from percentage of the protected animals relating to various doses (i.e. from the dose-response curve) by using probit analysis. The results are summarized in Table III.

TABLE III

| Compound No. | $ED_{50}$ p.o. mg/kg |
|---|---|
| 1 | 40.9 |
| 2 | 39.9 |
| 4 | 37.9 |

The compounds according to the invention showed a strong calcium-antagonizing and antihypoxic activity and had a low toxicity. Their oral $LD_{50}$ values (i.e. the does causing death of 50% of the animals) were found to be higher than 1000 mg/kg; thus, their therapeutic indices are favorable.

Thus, the invention relates to a method for the calcium uptake-inhibiting as well as antihypoxic and antianoxic treatment of mammals. This method comprises administering a prophylactically or therapeutically effective amount of a compound of the invention or a pharmaceutically acceptable acid addition or quaternary salt thereof to a patient suffering from anoxia connected with e.g. senile dementia, Alzheimer's disease, ischemic lesions, disturbances of the cognitive function, multi-infarctual dementia; hypoxia following atherosclerosis and the like. Depending on the severity of the disease and the condition of the patient, the daily dose amounts to 0.1 to 40 mg/kg which may be given once or in divided subdoses in oral, rectal or parenteral route.

The compounds according to the invention can be converted into pharmaceutical compositions in a known manner. The pharmaceutical compositions may be administered in oral, rectal and/or parenteral route. For oral administration, the composition may be formulated e.g. as a tablet, dragée or capsule. In order to prepare oral compositions, e.g. lactose or starch may be used as carriers. Gelatine, carboxymethylcellulose sodium, methylcellulose, polyvinylpyrrolidone or starch gum are suitable binding or granulating agents. As disintegrating agents, mainly potato starch or microcrystalline cellulose may be added though ultraamylopectin or formaldehyde-casein and the like are also useful. Talc, colloidal silicic acid, stearin, calcium or magnesium stearate and the like are suitable anti-adhesive and sliding agents. The liquid oral compositions of the invention can be prepared in the form of e.g. a suspension, syrup or elixir which may contain water, glycols, oils, alcohols as well as coloring and flavoring additives.

Tablets may be prepared e.g. by compression following the wet granulation. The mixture of the active ingredient with the carriers and optionally with a part of the disintegrating additive is granulated with an aqueous, alcoholic or aqueous-alcoholic solution of the binding agents in a suitable equipment, then the granulate is dried. Subsequently, after mixing the other disintegrating, sliding and anti-adhesive additives to the dried granulate, the mixture is compressed to tablets. If desired, the tablets may be provided with a groove in order to facilitate the administration. Tablets may also directly be prepared from a mixture containing the active ingredient and suitable additives. The tablets may optionally be converted to dragées by employing the commonly used pharmaceutical additives, e.g. protective, flavoring and coloring agents such as sugar, cellulose derivatives (methyl- or ethylcellulose, carboxymethylcellulose sodium and the like), polyvinylpyrrolidone, calcium phosphate, calcium carbonate, food dyes, dyeing lacquers, aromatizing agents, iron oxide pigments and the like. Capsulated compositions are prepared by filling a mixture of the active ingredient with the additives into capsules.

For rectal administration, the composition of the invention is formulated as a suppository containing a carrier mass, the so-called "adeps pro suppositorio" in addition to the active ingredient. As carriers, vegetable fats such as hardened vegetable oils, or triglycerides of $C_{12-18}$ fatty acids (preferably the carriers bearing the trade name Witepsol) may be used. The active ingredient is uniformly distributed in the molten carrier mass, then suppositories are prepared by moulding.

For parenteral administration, the composition of the invention is formulated as an injectable solution. For preparing these injectable solutions, the active ingredients are dissolved in distilled water and/or various organic solvents, e.g. glycol ethers, if desired, in the presence of solubilizing agents such as polyoxyethylene sorbitan monolaurate or monooleate or monostearate (Tween 20, Tween 60, Tween 80), respectively. The injectable solution may further contain various additives (auxiliary agents), e.g. preservatives such as ethylenediamine tetraacetate as well as pH-modifying and buffering substances or, if desired, a local anaesthetic agent such as lidocaine. Before filling into the ampouls, the injectable solution containing the composition of the invention is filtered and after filling in, it is subjected to sterilization.

On using the pharmaceutical composition of the invention, the patient is treated with a dose needed to ensure the desired effect. This dose depends upon several factors like the severity of the disease, the bodyweight of the patient and the route of administration. The dose to be used is in every case to be defined by the physician.

The invention also relates to a method for treating hypoxic brain damages of various origin such as the senile dementia, Alzheimer's disease hypoxia following atherosclerosis, multi-infarctual dementia and disturbances of the cognitive function. This method comprises administering a therapeutically effective amount of an active ingredient of the formula (I) or a pharmaceutically acceptable acid addition salt thereof to the patient.

The invention is illustrated in detail by the aid of the following non-limiting Examples.

EXAMPLE 1

Preparation of
1-oxa-2-oxo-3-propyl-4-methylene-8-[4,4-bis(4-fluorophenyl)butyl]-3,8-diazaspiro[4,5]-decane A mixture containing 8.4 g of 1-oxa-2-oxo-3-propyl-4-methylene-3,8-diazaspiro[4,5]decane. 22.4 g of 4,4-bis(4-fluorophenyl)butyl chloride, 16.6 g of anhydrous potassium carbonate and 0.3 g of potassium iodide in 90 ml of methyl isobutyl ketone is boiled under reflux and stirring for 8 hours, then the solvent is distilled off under reduced pressure. After adding benzene and water to the residue, the organic phase is separated, washed with water to neutral, dried over anhydrous magnesium sulfate and evaporated under reduced pressure. The crude product obtained is purified by chromatography on a silica gel column by using ethyl acetate for elution. The eluates are combined, evaporated and the residue is recrystallized from diisopropyl ether to give the title compound in 89% yield, m.p.: 107°-108° C.

Analysis: Calculated for $C_{27}H_{32}F_2N_2O_2$; C 71.34; H 7.10; F 8.36; N 6.16%; found: C 71.50; H 7.23; F 8.28; N 6.07%.

EXAMPLE 2

Preparation of
1-oxa-2-oxo-3-benzyl-4-methylene-8-[2-(4-fluorophenyl)ethylz)]-3,8-diazaspiro[4.5]decane A mixture containing 10.3 g of 1-oxa-2-oxo-3-benzyl-4-methylene-3,8-diazaspiro[4,5]decane, 16.2 g of 2-(4-fluorophenyl)ethyl bromide and 11.2 ml of triethylamine in 100 ml of methyl isobutyl ketone is refluxed under argon while stirring for 2.5 hours. After cooling down and adding water to the reaction mixture, the organic phase is separated, washed with saturate sodium chloride solution, dried over anhydrous sodium sulfate and evaporated under reduced pressure. The residue is recrystallized under clarifying by activated carbon from hexane and then from diisopropyl ether to obtain the title compound in 31.8% yield, m.p.: 100°-101° C.

Analysis: Calculated for $C_{23}H_{25}FN_2O_2$; C 72.61; H 6.62; F 4.99; N 7.36%; found: C 72.8; H 6.54; F 5.22; N 7.53%.

EXAMPLE 3

Preparation of
1-oxa-2-oxo-3-ethyl-4-methylene-8-(3,3-diphenylpropyl)-3,8-diazaspiro[4,7]decane hydrogen maleate A mixture containing 7.9 g of 1-oxa-2-oxo-3-ethyl-4-methylene-3,8-diazaspiro[4,5]decane, 26 g of 3,3-diphenyl-1-tosyloxypropane and 7.4 g of anhydrous sodium carbonate in 100 ml of methyl isopropyl ketone is refluxed under nitrogen while stirring for 5 hours. After evaporating the reaction mixture under reduced pressure, water is added to the residue and extracted with chloroform. The organic phase is washed with water, dried over anhydrous magnesium sulfate and evaporated under reduced pressure. The crude product is dissolved in acetone and the title salt is precipitated by adding an ethereal solution of maleic acid, m.p.: 168°-170° C.

The base can be liberated from the above salt by adding aqueous sodium hydroxide solution.

Analysis of the base: Calculated for $C_{25}H_{30}N_2O_2$; C 76.89; H 7.74; N 7.17%; found: C 76.95; H 7.89; N 7.24%.

EXAMPLE 4

Preparation of
1-oxa-2-oxo-3-decyl-4-hydroxy-4-methyl-8-[4,4-bis(4-fluorophenyl)buty]-3,8-diazaspiro-[4,5]decane hydrochloride 5.5 g of 1-oxa-2-oxo-3-decyl-4-methylene-8-[4,4-bis(4-fluorophenyl)butyl]-3,8-diazaspiro[4,5]decane are dissolved in 11 ml of formic acid and after dropping 100 ml of a 3 mol/liter hydrochloric acid to the solution under stirring, the reaction mixture is stirred for an additional 30 minutes. The crystals precipitated are filtered, washed with water and dried to give the title hydrochloride in 97.2% yield, m.p.: 109°-111° C. The base is liberated by adding aqueous sodium carbonate solution to the hydrochloride, extracted into chloroform, the organic phase is washed with water to neutral, dried over anhydrous sodium sulfate and evaporated under reduced pressure. After recrystallization from diisopropyl ether the base melts at 89°-90° C.

Analysis: Calculated for $C_{34}H_{48}F_2N_2O_3$; C 71.54; H 8.48; F 6.66; N 4.91%; Found: C 71.54; H 8.31; F 6.73; N 4.99%.

EXAMPLE 5

Preparation of
1-oxa-2-oxo-3-cyclohexyl-4-methylene-8-[2-(4-chlorophenyl)ethyl]-3,8-diazaspiro[4,5]-decane A mixture containing 8.14 g of 1-oxa-2-oxo-3-cyclohexyl-4-hydroxy-4-methyl-8-[2-(4-chlorophenyl)ethyl]-3,8-diazaspiro[4,5]decane and 0.8 g of p-toluenesulfonic acid monohydrate in 100 ml of xylene is boiled under stirring while the water formed in the reaction is azeotropically distilled out. The reaction is followed by using thin-layer chromatography. After termination of the reaction the mixture is cooled down, made alkaline by adding 5% by weight aqueous sodium hydroxide solution, then the organic phase is washed with water to neutral, dried over anhydrous sodium sulfate and evaporated under reduced pressure. After recrystallizing the crude product from ethanol the pure title product is obtained in 92.4% yield, m.p.: 134°–135° C.

Analysis: Calculated for $C_{22}H_{29}ClN_2O_2$; C 67.93; H 7.52; Cl 9.12; N 7.20%; found: C 67.88; H 7.65; Cl 9.25; N 7.11%.

EXAMPLE 6

Preparation of 1-oxa-2-oxo-3-methyl-4-methylene-8-(3-phenylpropyl)-3,8-diazaspiro[4.5]decane A solution of 7.5 g of 4-ethynyl-4-ethynyl-4-methylcarbamoyloxy-1-(3-phenylpropyl)piperidine in 100 ml of an ethanolic sodium ethoxide solution of 0.09 mol/liter concentration is refluxed under argon for 3 to 4 hours. After cooling down and adding aqueous ammonium chloride solution to the reaction mixture, the major part of the alcohol is distilled off under reduced pressure. The residue is diluted with water and extracted with benzene. The benzene phase is washed with water to neutral, dried over anhydrous magnesium sulfate and evaporated under reduced pressure. After recrystallizing the residue form hexane, the title compound is obtained in 68% yield, m.p.: 35°–36° C.

Analysis: Calculated for $C_{18}H_{24}N_2O_2$; C 71.97; H 8.05; N 9.33%; found: C 71.88; H 8.19; N 9.52%.

EXAMPLE 7

Preparation of 1-oxa-2-oxo-4-methylene-3-phenyl-8-(2-phenylethyl)-3,8-diazaspiro[4,5]decane A mixture containing 6.2 g of 4-acetyl-4-hydroxy-1-(2-phenylethyl)-piperidine, 2 ml of triethylamine and 11 ml of phenylisocyanate in 20 ml of xylene is refluxed under argon for 6 hours. After cooling down and diluting with xylene the reaction mixture is filtered and the filtrate is evaporated under reduced pressure. After recrystallizing the crude product form ethanol under clarifying by activated carbon, the title product is obtained in 49.4% yield, m.p.: 137°–138° C.

Analysis: Calculated for $C_{22}H_{24}N_2O_2$; C 75.83; H 6.94; N 8.04%; found: C 76.00; H 6.97; N 8.15%.

EXAMPLE 8

Preparation of 1-oxa-2-oxo-3-cyclohexyl-4-hydroxy-4-methyl-8-[2-(4-chlorophenyl)ethyl]-3,8-diazaspiro[4,5]decane hydrochloride 10.7 g of 1-oxa-2-oxo-3-cyclohexyl-4-hydroxy-4-methyl-3,8-diazaspiro[4,5]decane are refluxed with 13.2 g of 2-(4-chlorophenyl)ethyl bromide, 8.2 g of anhydrous powdered potassium carbonate and 0.7 g of potassium iodide in 110 ml of methyl isobutyl ketone under nitrogen while stirring for 6 hours. After evaporating the solvent under reduced pressure and adding water to the residue, the mixture is extracted with benzene. The combined benzene solution is washed with water to neutral, dried over anhydrous sodium sulfate, then the benzene solution is filtered through an aluminum oxide layer and evaporated under reduced pressure. After recrystallization of the residue from hexane, the base is converted to the hydrochloride by adding hydrogen chloride in diisopropyl ether solution. Thus, the title hydrochloride is obtained in 58.4% yield with a decomposition point of 310°–315° C.

Analysis of the base: Calculated for $C_{22}H_{31}ClN_2O_3$; C 63.93; H 7.68; Cl 8.71; N 6.88%; found: C 65.10; H 7.53; Cl 8.60; N 7.00%.

By using the appropriate starting substances the following compounds are prepared in an analogous manner as described in Examples 1 to 3 or 8.

1-Oxa-2-oxo-3-methyl-4-methylene-8-(2-phenylethyl)-3,8-diazaspiro[4,5]decane, m.p.: 119°–120° C.;

1-Oxa-2-oxo-4-methylene-3-phenyl-8-[2-(4-chlorophenyl)-ethyl]-3,8-diazaspiro[4,5]decane, m.p.: 134°–135° C.;

1-Oxa-2-oxo-3-ethyl-4-methylene-8-[2-(4-methylphenyl)-ethyl]-3,8-diazaspiro[4,5]decane hydrochloride, decomp. at 280°–282° C.;

1-Oxa-2-oxo-3-cyclohexyl-4-methylene-8-[2-(4-fluorophenyl)-ethyl[-3,8-diazaspiro[4,5]decane, m.p.: 125°–126° C.;

1-Oxa-2-oxo-4-methylene-3-phenyl-8-[2-(4-fluorophenyl)-ethyl]-3,8-diazaspiro[4,5]decane, m.p.: 145°–147° C.;

1-Oxa-2-oxo-3-ethyl-4-methylene-8-(2-phenylethyl)-3,8-diazaspiro[4,5]decane, m.p.: 121°–122° C.;

1-Oxa-2-oxo-3-tert-butyl-4-methylene-8-[4,4-bis(4-fluorophenyl)butyl]-3,8-diazaspiro[4,5]decane, m.p.: 90°–92° C.;

1-Oxa-2-oxo-3-isopropyl-4-methylene-8-[4,4-bis(4-fluorophenyl)butyl]-3,8-diazaspiro[4,5]decane, m.p.: 118°–119° C.;

1-Oxa-2-oxo-3-methyl-4-methylene-8-[4,4-bis(4-fluorophenyl)butyl]-3,8-diazaspiro[4,5]decane, m.p.: 90°–91° C.;

1-Oxa-2-oxo-3-tert-butyl-4-methylene-8-(2-phenylethyl)-3,8-diazaspiro[4,5]decane, m.p.: 106°–107° C.;

1-Oxa-2-oxo-3-isopropyl-4-methylene-8-[2-(4-chlorophenyl)-ethyl]-3,8-diazaspiro[4,5]decane, m.p.: 101°–102° C.;

1-Oxa-2-oxo-3-methyl-4-methylene-8-[2-(4-fluorophenyl)-ethyl]-3,8-diazaspiro[4,5]decane, m.p.: 74°–75° C.;

1-Oxa-2-oxo-3-ethyl-4-methylene-8-[4,4-bis(4-fluorophenyl)-butyl]-3,8-diazaspiro[4,5]decane, m.p.: 111°–112° C.;

1-Oxa-2-oxo-3-isopropyl-4-methylene-8-[2-(4-fluorophenyl)-etyl]-3,8-diazaspiro[4,5]decane, m.p.: 103°–104° C.;

1-Oxa-2-oxo-4-methylene-3-phenyl-8-[4,4-bis(4-fluorophenyl)-butyl]-3,8-diazaspiro[4,5]decane, m.p.: 125°–126° C.;

1-Oxa-2-oxo-4-methylene-3-propyl-8-[2-(4-fluorophenyl)-ethyl]-3,8-diazaspiro[4,5]decane, m.p.: 78°–79° C.;

1-Oxa-2-oxo-3-[2-(3,4-dimethoxyphenyl)ethyl]-4-methylene-8-(2-phenylethyl)-3,8-diazaspiro[4,5]decane, m.p.: 114°–115° C.;

1-Oxa-2-oxo-3-benzyl-4-methylene-8-[4,4-bis(4-fluorophenyl)butyl]-3,8-diazaspiro[4,5]decane, m.p.: 81°–82° C.;

1-Oxa-2-oxo-3-decyl-4-methylene-8-[4,4-bis(4-fluorophenyl)butyl]-3,8-diazaspiro[4,5]decane hydrogen maleate, m.p.: 106°–107° C.;

1-Oxa-2-oxo-3-cyclohexyl-4-methylene-8-[4,4-bis(4-fluorophenyl)butyl]-3,8-diazaspiro[4,5]decane, m.p.: 121°–122° C.;

1-Oxa-2-oxo-3-butyl-4-methylene-8-(2-phenylethyl)-3,8-diazaspiro[4,5]decane, m.p.: 70°–71° C.;

1-Oxa-2-oxo-3-methyl-4-methylene-8-[2-(4-chlorophenyl)-ethyl]-3,8-diazaspiro[4,5]decane, m.p.: 118°–119° C.;

1-Oxa-2-oxo-3-tert-butyl-4-methylene-8-[2-(4-chlorophenyl)-ethyl]-3,8-diazaspiro[4,5]decane, m.p.: 104°–105° C.;

1-Oxa-2-oxo-3-ethyl-4-methylene-8-[2-(4-fluorophenyl)-ethyl]-3,8-diazaspiro[4,5]decane, m.p.: 83°–84° C.;

1-Oxa-2-oxo-3-methyl-4-methylene-8-[2-(3,4-dimethoxyphenyl)ethyl]-3,8-diazaspiro[4,5]decane hydrochloride, m.p.: 278°–280° C.; and 1-Oxa-2-oxo-3-tert-butyl-4-methylene-8-[2-(4-fluorophenyl)-ethyl]-3,8-diazaspiro[4,5]decane, m.p.: 93°–94° C.

EXAMPLE 9

Preparation of 1-oxa-2-oxo-4-methylene-3-(1-naphthyl)-8-[2-(4-fluorophenyl)ethyl]-3,8-diazaspiro[4,5]-decane 9.9 g of 4-ethynyl-4-hydroxyl-1-[2-(4-fluorophenyl)-ethyl]piperidine are heated with 7.0 ml of 1-naphthyl isocyanate under argon. A violet exothermic reaction occurs. The temperature is maintained between 170° C. and 180° C. by external cooling for one hour. After cooling down and dissolving the solid residue in chloroform, the solution is filtered through an aluminum oxide layer and the filtrate is evaporated under reduced pressure. After recrystallizing the residue form ethanol the title compound is obtained in 65% yield, m.p.: 160°–161° C.

Analysis: Calculated for $C_{26}H_{25}FN_2O_2$: C 74.98; H 6.05; F 4.56; N 6.73%; found: C 75.10; H 6.25; F 4.37; N 6.55%.

EXAMPLE 10

Preparation of 1-oxa-2-oxo-3-n-butyl-4-methylene-8-[4,4-bis(4-fluorophenyl)butyl]-3,8-diazaspiro[4,5]-decane 3.3 g of n-butyl isocyanate dissolved in 11 ml of benzene are portionwise added to a gently boiling suspension containing 11 g of 4-ethynyl-4-hydroxy-1-[4,4-bis(4-fluorophenyl)butyl]piperidine and 0.09 g of sodium methoxide in 45 ml of benzene under argon while stirring, then the mixture is refluxed for an additional 3 to 4 hours. After cooling down the benzene solutin is washed with water, dried over anhydrous sodium sulfate, filtered and the solvent is distilled off under reduced pressure. After recrystallizing the residue from diisopropyl ether the title compound is obtained in 79.5% yield, m.p.: 94°–95° C.

Analysis: Calculated for $C_{28}H_{34}F_2N_2O_2$: C 71.77; H 7.31; F 8.11; N 5.98%; found: C 71.98; H 7.40; F 8.24; N 6.13%.

EXAMPLE 11

Preparation of 1-oxa-2-oxo-3-butyl-4-methylene-8-[2-(4-chlorophenyl)ethyl]-3,8-diazaspiro[4,5]-decane 13.2 g of 4-ethynyl-4-hydroxy-1-[2-(4-chlorophenyl)ethyl]piperidine are refluxed with 6.5 g of n-butyl isocyanate in 40 ml of 2-picoline in the presence of 0.2 g of anhydrous potassium acetate under argon for 6 hours. After evaporating the solvent under reduced pressure and dissolving the residue in benzene, the organic phase is washed with water and dried over anhydrous sodium sulfate. The benzene solution is filtered through an aluminum oxide layer and evaporated under reduced pressure. After recrystallizing the crude product from hexane the title compound is obtained in 74.5% yield, m.p.: 86°–87° C.

Analysis: Calculated for $C_{20}H_{27}ClN_2O_2$: C 66.19; H 7.50; Cl 9.77; N 7.72%; found: C 66.23; H 7.57; Cl 9.90; N 7.64%.

The following compounds are prepared similarly as described in Examples 9, 10 or 11 by using the appropriate starting substances:

1-Oxa-2-oxo-4-methylene-3-propyl-8-[2-(4-chlorophenyl)-ethyl]-3,8-diazaspiro[4,5]decane, m.p.: 82°–83° C.;

1-Oxa-2-oxo-3-ethyl-4-methylene-8-[2-(4-chlorophenyl)-ethyl]-3,8-diazaspiro[4,5]decane, m.p.: 106°–107° C.;

1-Oxa-2-oxo-4-methylene-3-(1-naphthyl)-8-[4,4-bis(4-fluorophenyl)butyl]-3,8-diazaspiro[4,5]decane, m.p.: 127–°128° C.;

1-Oxa-2-oxo-3-tert-butyl-4-methylene-8-[4,4-bis(4-fluorophenyl)butyl]-3,8-diazaspiro[4,5]decane, m.p.: 90°–92° C.;

1-Oxa-2-oxo-3-heptyl-4-methylene-8-[4,4-bis(4-fluorophenyl)butyl]-3,8-diazaspiro[4,5]decane hydrogen maleate, m.p.: 121°–122° C.;

1-Oxa-2-oxo-3-(3,4-dichlorophenyl)-4-methylene-8-[2-(4-chlorophenyl)ethyl]-3,8-diazaspiro[4,5]decane hydrochloride, decomp. at 292°–295° C.;

1-Oxa-2-oxo-3-cyclohexyl-4-methylene-8-(2-phenylethyl)-3,8-diazaspiro[4,5]decane, m.p.: 152°–153° C.;

1-Oxa-2-oxo-4-methylene-3-propyl-8-(2-phenylethyl)-3,8-diazaspiro[4,5]decane, m.p.: 97°–98° C.; and 1-Oxa-2-oxo-3-butyl-4-methylene-8-[2-(4-fluorophenyl)ethyl]-3,8-diazaspiro[4,5]decane, m.p.: 91°–92° C.

EXAMPLE 12

Preparation of 1-oxa-2-oxo-3-butyl-4-hydroxy-4-methyl-8-[4,4-bis(4-fluorophenyl)butyl]-3,8-diazaspiro[4,5]decane hydrochloride 3 ml of butylamine dissolved in 3 ml of benzene are dropped to a solution of 8.3 g of 1,3-dioxa-2-oxo-4-methylene-8-[4,4-bis(4-fluorophenyl)butyl]-8-azaspiro[4,5]decane in 17 ml of anhydrous benzene under stirring. Meanwhile the temperature of the reaction mixture raises to 38° to 45° C. Thereafter the reaction mixture is stirred at room temperature for an additional 16 hours, then evaporated under reduced pressure. After take up of the residue in anhydrous ether the title hydrochloride salt is precipitated by adding ethereal hydrogen chloride solution. The title salt is obtained in 87% yield, m.p.: 218°–221° C.

The base is obtained from the hydrochloride by adding ammonium hydroxide solution.

Analysis of the base: Calculated for $C_{28}H_{36}F_2N_2O_3$; C 69.11; H 7.46; F 7.81; N 9.86%; found: C 69.2; H 7.50; F 7.64; N 9.72%.

EXAMPLE 13

Preparation of 1-oxa-2-oxo-3-methyl-4-methylene-8,8-bis(3-phenylpropyl)-3,8-diazaspiro[4,5]decan-8-ium iodide 6.0 g of 1-oxa-2-oxo-3-methyl-4-methylene-8-(3-phenylpropyl)-3,8-diazaspiro[4,5]decane are refluxed with 5.4 g of 3-phenylpropyl iodide in 60 ml of methyl isobutyl ketone under nitrogen for 4 hours, then the solvent is distilled off under reduced pressure. After adding hexane to the residue the solid precipitate is filtered and recrystallized from ethanol to give the title compound in 86% yield, m.p.: 219°–220° C.

EXAMPLE 14

Preparation of
1,3-dioxa-2-oxo-4-methylene-8-[4,4-bis(4-fluorophenyl)-butyl]-8-azaspiro[4,5]decane hydrogen maleate A solution of 16.0 g of 1-[4,4-bis(4-fluorophenyl)-butyl]-4-butyl-carbamoyloxy-4-ethynylpiperidine in 90 ml of anhydrous dioxane is saturated by dry gaseous hydrogen chloride at 15° to 20° C., then the reaction mixture is left to stand overnight. The solvent is evaporated at 40° to 50° C. under reduced pressure. After adding water to the residue, the base is liberated with sodium hydrogen carbonate and extracted into benzene. The benzene solution is dried over anhydrous magnesium sulfate, then the solvent is evaporated under reduced pressure. After dissolving the residue in ethyl acetate, the solution is filtered through a silica gel column and the solution thus obtained is evaporated under reduced pressure. After taking up the residue in acetone, the title hydrogen maleate salt is precipitated by maleic acid. The title salt is obtained in 55% yield, m.p.: 149°–150° C.

Analysis for the base: Calculated for $C_{24}H_{25}F_2NO_3$; C 69.72; H 6.09; F 9.19; N 3.39%; found: C 69.83; H 6.17; F 9.35; N 3.12%.

EXAMPLE 15

Preparation of
1-oxa-2-oxo-3,4-dimethyl-4-hydroxy-8-(2-phenylethyl)-3,8-diazaspiro[4,5]decane A solution containing 9.1 g of 4-acetyl-4-methylcarbamoyloxy-1-(2-phenylethyl)piperidine and 0.5 g sodium methoxide in 100 ml of methanol is refluxed under argon for 4 for 5 hours. After cooling down the sodium methoxide is decomposed by adding aqueous ammonium chloride solution, the mixture is diluted with water and methanol is distilled off under reduced pressure. After filtration the precipitate obtained is recrystallized from ethanol to give the title product in 72.1% yield, m.p.: 184°–185° C.

Analysis: Calculated for $C_{17}H_{24}N_2O_3$; C 67.08; H 7.95; N 9.20%; found: C 67.11; H 7.90; N 9.03%.

EXAMPLE 16

Preparation of
1-oxa-2-oxo-3-benzyl-4-hydroxy-4-methyl-8-[2-(4-fluorophenyl)ethyl]-3,8-diazaspiro[4,5]decane hydrochloride A solution of 6.1 g of 1-oxa-2-oxo-3-benzyl-4-methylene-8-[2-(4-fluorophenyl)ethyl]-3,8-diazaspiro[4,5]decane in 120 ml of 0.2 molar hydrochloric acid is refluxed for 10 minutes and then evaporated to a volume of 70 ml under reduced pressure. The mixture is cooled at 1° to 5° C. for 30 minutes, then the crystalline precipitate is filtered and dried to give the title hydrochloride in 98% yield, decomp. at 295° C.

The base is liberated from the hydrochloride by adding aqueous ammonium hydroxide solution.

Analysis for the base: Calculated for $C_{23}H_{27}FN_2O_3$; C 69.32; H 6.83; F 4.77; N 7.03%; found: C 69.40; H 6.64; F 4.85; N 7.16%.

The following compounds are prepared similarly as described in the Example 12 or 16 by using the appropriate starting substances:

1-Oxa-2-oxo-3,4-dimethyl-4-hydroxy-8-[2-(4-fluorophenyl)-ethyl]-3,8-diazaspiro[4,5]decane, m.p.: 197°–198° C.;

1-Oxa-2-oxo-3-cyclohexyl-4-hydroxy-4-methyl-8-[2-(4-fluorophenyl)ethyl]-3,8-diazaspiro[4,5]decane, m.p.: 189°–190° C.;

1-Oxa-2-oxo-3-tert-butyl-4-hydroxy-4-methyl-8-[2-(4-fluorophenyl)ethyl]-3,8-diazaspiro[4,5]decane hydrochloride, decomp. at 286°–288° C.;

1-Oxa-2-oxo-3,4-dimethyl-4-hydroxy-8-[4,4-bis(4-fluorophenyl)butyl]-3,8-diazaspiro[4,5]decane hydrochloride, decomp. at 220°–223° C.;

1-Oxa-2-oxo-3-benzyl-4-hydroxy-4-methyl-8-[4,4-bis(4-fluorophenyl)butyl]-3,8-diazaspiro[4,5]decane hydrochloride, decomp. at 177°–179° C.;

1-Oxa-2-oxo-4-hydroxy-3-isopropyl-4-methyl-8-[2-(4-fluorophenyl)ethyl]-3,8-diazaspiro[4,5]decane, m.p.: 157°–158° C.;

1-Oxa-2-oxo-4-hydroxy-4-methyl-3-phenyl-8-[4,4-bis(4-fluorophenyl)butyl]-3,8-diazaspiro[4,5]decane hydrochloride, decomp. at 274°–276° C.;

1-Oxa-2-oxo-3-butyl-4-hydroxy-4-methyl-8-[2-(4-fluorophenyl)ethyl]-3,8-diazaspiro[4,5]decane, m.p.: 155°–156° C.;

1-Oxa-2-oxo-4-hydroxy-4-methyl-3-propyl-8-[2-(4-fluorophenyl)ethyl]-3,8-diazaspiro[4,5]decane hydrochloride, decomp. at 248° C.; the base melts at 138°–139° C.;

1-Oxa-2-oxo-3-ethyl-4-hydroxy-4-methyl-8-[4,4-bis(4-fluorophenyl)butyl]-3,8-diazaspiro[4,5]decane hydrochloride, decomp. at 235° C.;

1-Oxa-2-oxo-4-hydroxy-4-methyl-3-(1-naphthyl)-8-[4,4-bis(4-fluorophenyl)butyl]-3,8-diazaspiro[4,5]decane hydrochloride, decomp. at 180°–182° C.;

1-Oxa-2-oxo-3-heptyl-4-hydroxy-4-methyl-8-[4-bis(4-fluorophenyl)butyl]-3,8-diazaspiro[4,5]decane, m.p.: 128°–129° C.;

1-Oxa-2-oxo-4-hydroxy-4-methyl-3-(1-naphthyl)-8-[2-(4-fluorophenyl)ethyl]-3,8-diazaspiro[4,5]decane hydrochloride, decomp. at 288°–290° C.;

1-Oxa-2-oxo-3-ethyl-4-hydroxy-4-methyl-8-[2-(4-fluorophenyl)ethyl]-3,8-diazaspiro[4,5]decane, m.p.: 139°–140° C.;

1-Oxa-2-oxo-3-cyclohexyl-4-hydroxy-4-methyl-8-[4,4-bis(4-fluorophenyl)butyl]-3,8-diazaspiro[4,5]decane hydrochloride, decomp. at 258° to 260° C.;

1-Oxa-2-oxo-4-hydroxy-3-isopropyl-4-methyl-8-[4,4-bis(4-fluorophenyl)butyl]-3,8-diazaspiro[4,5]decane hydrochloride, decomp. at 251°–253° C.;

1-Oxa-2-oxo-3-butyl-4-hydroxy-4-methyl-8-[4,4-bis(4-fluorophenyl)butyl]-3,8-diazaspiro[4,5]decane hydrochloride, decomp. at 218°–220° C.;

1-Oxa-2-oxo-4-hydroxy-4-methyl-3-propyl-8-[4,4-bis(4-fluorophenyl)butyl]-3,8-diazaspiro[4,5]decane hydrochloride, decomp. at 134°–136° C.;

1-Oxa-2-oxo-4-hydroxy-4-methyl-3-phenyl-8-[2-(4-fluorophenyl)ethyl]-3,8-diazaspiro[4,5]decane hydrochloride, decomp. at 346°–350° C.;

1-Oxa-2-oxo-3-(3,4-dichlorobenzyl)-4-hydroxy-4-methyl-8-[2-(4-chlorophenyl)ethyl]-3,8-diazaspiro[4,5]decane hydrochloride, decomp. at 310°–315° C.; and 1-Oxa-2-oxo-4-hydroxy-4-methyl-8-[4,4-bis(4-fluorophenyl)-butyl]-3,8-diazaspiro[4,5]decane hydrochloride, m.p.: 130°–132° C.

EXAMPLE 17

Preparation of
4-ethynyl-4-hydroxyl-1-[4,4-bis(4-fluorophenyl)butyl]-piperidine hydrochloride Acetylene is introduced into a solution containing 38.4 g of potassium tert-butoxide in 250 ml of tetrahydrofuran at a temperature between 0° C. and −5° C. under stirring for 30 minutes, then 78.0 g of 1-[4,4-bis(4-fluorophenyl)butyl]-4-piperidone dissolved in 200 ml of tetrahydrofuran are dropwise added and acetylene is introduced for an additional one hour. Thereafter the reaction mixture is cooled to −10° C. and saturated aqueous ammonium chloride solution is added under nitrogen. After evaporating tetrahydrofuran under reduced pressure, the residue is extracted with benzene. The benzene solution is washed with water, dried over anhydrous magnesium sulfate and evaporated under reduced pressure. After taking up the residue in acetone, the hydrochloride is precipitated by adding hydrogen chloride in diisopropyl ether solution. The title hydrochloride is obtained in 91.0% yield, m.p.: 166°–168° C.

Analysis for the base: Calculated for $C_{23}H_{25}F_2NO$; C 74.77; H 6.82; F 10.28; N 3.79%; found: C 74.85; H 6.66; F 10.15; N 4.00%.

EXAMPLE 18

Preparation of
4-butylcarbamoyloxy-4-ethynyl-1-[4,4-bis(4-fluorophenyl)butyl]piperidine hydrochloride 6.4 ml of butyl isocyanate dissolved in 19 ml of benzene are dropwise added to a mixture of 18.5 g of 4-ethynyl-4-hydroxy-1-[4,4-bis(4-fluorophenyl)butyl]-piperidine, 0.35 g of anhydrous powdered potassium carbonate and 74 ml of benzene in a nitrogen atmosphere under reflux and stirring. The mixture is refluxed for additional one hour, then cooled down and water is added. After separating the phases the benzene solution is washed with water to neutral, dried over anhydrous magnesium sulfate, the solution is filtered through a silica gel column and evaporated under reduced pressure. After taking up the residue in diisopropyl ether, the hydrochloride salt is precipitated by adding hydrogen chloride in diisopropyl ether solution. The title hydrochloride is obtained in 87.5%, m.p.: 84°–89° C.

Analysis of the base: Calculated for $C_{28}H_{34}F_2NO_2$; C 71.77; H 7.31; F 8.11; N 5.98%; found: C 71.88; H 7.50; F 8.28; N 5.83%.

EXAMPLE 19

Preparation of
4-acetyl-4-hydroxy-1-[4,4-bis(4-fluorophenyl)butyl]-piperidine hydrochloride A solution of 1,3-dioxa-2-oxo-4-methylene-8-[4,4-bis(4-fluorophenyl)butyl]-8-azaspiro[4,5]decane in 100 ml of a 2.8 molar sodium hydroxide solution is stirred at 80° to 90° C. under argon. After cooling down the reaction mixture is extracted with benzene, the benzene layer is washed with water to neutral, dried over anhydrous sodium sulfate, then the solvent is distilled off under reduced pressure. The evaporation residue is dissolved in diisopropyl ether and the hydrochloride is precipitated by adding hydrogen chloride in diisopropyl ether solution. The title hydrochloride is obtained in 61% yield, m.p.: 62°–67° C.

Analysis of the base: Calculated for $C_{23}H_{27}F_2NO_2$; C 71.29; H 7.02; F 9.81; N 3.61%; found: C 71.27; H 7.18; F 9.63; N 3.80%.

EXAMPLE 20

Pharmaceutical compositions containing e.g. the following components (ingredients) can be prepared from the compounds according to the invention.

a) Preparation of Tablets 50.0 g of active ingredient are mixed together with 92 g of lactose 40 g of potato starch, 4 g of polyvinylpyrrolidone, 6 g of talc, 1 g of magnesium stearate, 1 g of colloidal silicon dioxide (Aerosil) and 6 g of ultraamylopectin and, after wet granulation, the product obtained is compressed to tablets containing 50 mg of the active ingredient each.

b) Preparation of Dragées

The tablets prepared as described above are covered in a manner known per se with a coating consisting of sugar and talc. The dragées are polished by using a mixture of bee's wax and carnaube wax. Each dragée weighs 250 mg.

c) Preparation of Capsules 100 mg of active ingredient, 30 g of sodium lauryl sulfate, 280 g of starch, 280 g of lactose, 4 g of colloidal silicon dioxide (Aerosil) and 6 g of magnesium stearate are thoroughly mixed together and after sieving, the mixture obtained is filled into hard gelatine capsules containing 20 mg of the active ingredient each.

d) Preparation of Suppositories 30.0 mg of active ingredient are thoroughly mixed with 60.0 mg of lactose. Simultaneously, 1910.0 mg of suppository base (e.g. Witepsol 4) are molten (all weights are calculated for one suppository), cooled to 35° C. and the mixture of the active ingredient and lactose are mixed thereto by using a homogenizer. The product obtained is poured into cooled conic moulds. Each suppository weights 2000 mg.

e) Preparation of a Suspension

Components in 100 ml of the suspension:

| | |
|---|---|
| Actve ingredient | 1.00 g |
| Sodium hydroxide | 0.26 g |
| Citric acid | 0.30 g |
| Nipagin (metyl 4-hydroxybenzoate sodium salt) | 0.10 g |
| Carbopol 940 (polyacrylic acid) | 0.30 g |
| 96% Ethanol | 1.00 g |
| Raspberry flavor | 0.60 g |
| Sorbitol aqueous solution of 70%) | 71.00 g |
| Distilled water for injection purpose up to | 100.00 ml |

After adding carbopol in little portions to the solution of nipagin and citric acid in 20 ml of distilled water under vigorous stirring, the solution obtained is left to stand for 10 to 12 hours. Subsequently, the amount given above of sodium hydroxide dissolved in 1 ml of distilled water, the aqueous solution of sorbitol and finally the ethanolic solution of the raspberry flavor are dropped in under stirring. The active ingredient is added in small portions to this mixture and suspended by using a submerged homogenizer. Finally, the suspension is supplemented to 100 ml by adding distilled water and the syrupy suspension is led through a colloid mill.

What is claimed is:

1. A compound of the formula (I),

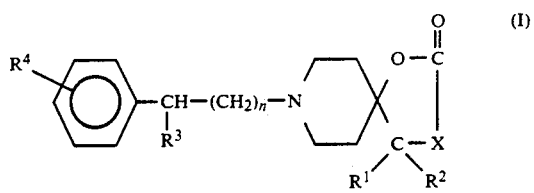

wherein

X means oxygen or an NR group, wherein
R stands for hydrogen, a $C_{1-12}$alkyl, $C_{3-6}$cycloalkyl, carbocyclic $C_{6-10}$aryl or carbocyclic $C_{6-10}$aryl-$C_{1-4}$alkyl group, the latter two groups are unsubstituted or substituted on their aromatic moiety by at least one same or different halogen, $C_{1-4}$alkyl or $C_{1-4}$alkoxy group;

$R^1$ and $R^2$ together represent a methylene group or, when X stands for an NR group, one of $R^1$ and $R^2$ may represent a hydroxyl group whereas the other is a methyl group;

$R^3$ stands for hydrogen or a phenyl group unsubstituted or substituted by at least one halogen, $C_{1-4}$alkyl, $C_{1-4}$alkoxy or hydroxyl group;

$R^4$ means hydrogen, or at least one halogen, $C_{1-4}$alkyl, $C_{1-4}$alkoxy, hydroxyl or trihalomethyl group; and n is 1, 2 or 3 or a pharmaceutically acceptable acid addition or quaternary ammonium salt thereof.

2. A compound of the formula (I) defined in claim 1 and selected from the group consisting of 1-oxa-2-oxo-3-tert-butyl-4-methylene-8-(4,4-bis(4-fluoro-phenyl)-butyl)-3,8-diazaspiro{4,5}decane, 1-oxa-2-oxo-3-cyclohexyl-4-methylene-8-{4,4-bis(4-fluorophenyl)butyl}-3,8-diazaspiro{4,5}decane,
1-oxa-2-oxo-3-butyl-4-hydroxy-methyl-8-{4,4-bis(4-fluorophenyl)butyl}-3,8-diazaspiro{4,5}decane.
1-oxa-2-oxo-4-methylene-3-phenyl-8-{4,4-bis(4-fluorophenyl)-butyl}-3,8-diazaspiro{4,5}decane,
1-oxa-2-oxo-4hydroxy-4-methyl-3-propyl-8-(2-(4-fluorophenyl)ethyl)-3,8-diazaspiro{4,5}decane,
1,3-dioxa-2-oxo-4-methylene-8-{4,4-bis(4-fluoro-phenyl)-butyl}-8-azaspiro{4,5}decane,
1-oxa-2-oxo-3-cyclohexyl-4-hydroxy-4-methyl-8-{2-(4-fluorophenyl)ethyl}-3,8diazaspiro{4,5}decane, and 1-oxa-2-oxo-3-ethyl-4-hydroxy-4-methyl-8-{2-(4-fluorophenyl)-ethyl}-3,8-diazaspiro{4,5}decane;

or a pharmaceutically acceptable acid addition or quaternary ammonium salt thereof.

3. 1-oxa-2-oxo-3-butyl-4-methylene-8-{4,4-bis-(4-fluorophenyl)butyl}-3,8-diazaspiro{4,5}decane as defined in claim 1 or a pharmaceutically acceptable salt thereof.

4. 1-oxa-2-oxo-3-tert-butyl-4-methylene-8-{4,4-bis-(4-fluorophenyl)butyl}-3,8-diazaspiro{4,5}decane as defined in claim 1 or a pharmaceutically acceptable salt thereof.

5. 1-oxa-2-oxo-3-phenyl-4-methylene-8-{4,4-bis-(4-fluorophenyl)butyl}-3,8-diazaspiro{4,5}decane as defined in claim 1 or a pharmaceutically acceptable salt thereof.

6. 1-oxa-2-oxo-3-cyclohexyl-4-methylene-8-{4,4-bis-(4-fluorophenyl)butyl}-3,8-diazaspiro{4,5}decane as defined in claim 1 or a pharmaceutically acceptable salt thereof.

7. 1-oxa-2-oxo-3-butyl-4-hydroxy-4-methyl-8-{4,4-bis-(4-fluorophenyl)butyl}-3,8-diazaspiro{4,5}decane as defined in claim 1 or a pharmaceutically acceptable salt thereof.

8. 1-oxa-2-oxo-3,4-diemthyl-4-hydroxy-8-(2-{4-fluorophenyl)ethyl}-3,8-diazaspiro{4,5}decane as defined in claim 1 or a pharmaceutically acceptable salt thereof.

9. 1-oxa-2-oxo-3-propyl-4-hydroxy-4-methyl-8-{2-(4-fluoro-phenyl)ethyl}-3,8diazaspiro{4,5}decane as defined in claim 1 or a pharmaceutically acceptable salt thereof.

10. 1-oxa-2-oxo-3-cyclohexyl-4-hydroxy-4-methyl-8-{2-(4-fluoro-phenyl)ethyl}-3,8-diazaspiro{4,5}decane as defined in claim 1 or a pharmaceutically acceptable salt thereof.

11. 1-oxa-2-oxo-3-ethyl-4-hydroxy-4-methyl-8-{2-(4-fluoro-phenyl)ethyl}-3,8-diazaspiro{4,5}decane as defined in claim 1 or a pharmaceutically acceptable salt thereof.

12. An antihypoxic and antianoxic pharmaceutical composition for treating brain damage, which comprises as active ingredient a therapeutically effective amount of the compound of the formula (I) as defined in claim 1 or a pharmaceutically acceptable acid addition or quaternary ammonium salt thereof in admixture with a pharmaceutically acceptable inert carrier.

13. A method for the calcium uptake-inhibiting as well as antihypoxic and antianoxic treatment of a mammal suffering from brain damage, which comprises administering to the mammal to be treated a therapeutically effective dose of a compound of the formula (I) as defined in claim 1, or a pharmaceutically acceptable acid addition or quaternary ammonium salt thereof alone or in the form of a pharmaceutical composition.

* * * * *